(12) United States Patent
Arai

(10) Patent No.: US 7,063,643 B2
(45) Date of Patent: Jun. 20, 2006

(54) PHYSICAL TRAINING MACHINE OPERATION SYSTEM AND METHOD

(75) Inventor: Kazuhiko Arai, Saitama (JP)

(73) Assignee: Combi Corporation, Tokyo-to (JP)

( * ) Notice: Subject to any disclaimer, the term of this patent is extended or adjusted under 35 U.S.C. 154(b) by 425 days.

(21) Appl. No.: 10/092,559

(22) Filed: Mar. 8, 2002

(65) Prior Publication Data

US 2002/0128119 A1    Sep. 12, 2002

(30) Foreign Application Priority Data

Mar. 8, 2001 (JP) .............................. 2001-65171

(51) Int. Cl.
*A63B 21/00* (2006.01)
(52) U.S. Cl. .................... 482/8; 482/1; 482/9; 482/900
(58) Field of Classification Search ................ 482/1–9, 482/51, 54, 900–902
See application file for complete search history.

(56) References Cited

U.S. PATENT DOCUMENTS

| | | | |
|---|---|---|---|
| 6,152,856 A | 11/2000 | Studor et al. | |
| 6,458,060 B1 * | 10/2002 | Watterson et al. | 482/54 |
| 6,607,483 B1 * | 8/2003 | Holland | 600/300 |
| 6,645,124 B1 * | 11/2003 | Clem | 482/4 |
| 6,702,719 B1 * | 3/2004 | Brown et al. | 482/8 |
| 6,740,007 B1 * | 5/2004 | Gordon et al. | 482/9 |
| 6,808,472 B1 * | 10/2004 | Hickman | 482/8 |

FOREIGN PATENT DOCUMENTS

| | | |
|---|---|---|
| WO | 87/05727 A1 | 9/1987 |
| WO | 91/07214 A1 | 5/1991 |
| WO | 01/12269 A1 | 2/2001 |

* cited by examiner

*Primary Examiner*—Glenn E. Richman
(74) *Attorney, Agent, or Firm*—Birch, Stewart, Kolasch & Birch, LLP

(57) ABSTRACT

The physical training machine operation system of the present invention is adapted to inexpensively provide up-to-date exercise programs making use of results of medical science, exercise physiology and other sciences, specifically for individual users. A health promotion facility (10) is equipped with a plurality of training machines (12) connected to each other via a private network (11). Each training machine (12) is connected to an external network (22) via a private server (13). In a home (20), a training machine (21) connected to the external network (22) is installed, and a management server (31) connected to the external network (22) is installed in an operation business entity's facility (30). The management server (31) holds different kinds of exercise programs to be used in the training machines (12, 21) to select a specific exercise program from the different kinds of exercise programs in response to a user's request and supply the selected exercise program to the training machine (12, 21) through the external network (22) and the private network (11).

17 Claims, 5 Drawing Sheets

PHYSICAL TRAINING MACHINE OPERATION SYSTEM AND METHOD

BACKGROUND OF THE INVENTION

1. Field of the Invention

The present invention relates to physical training machines used in health promotion facilities like sports clubs and in homes of individuals, and especially to a physical training machine operation system and a method adapted to present up-to-date exercise programs making use of results of medical science, exercise physiology, and so on, inexpensively and specifically for individual users.

2. Description of the Related Art

Along with increased recent anxiety for health and necessity of health promotion activities toward the aging society, more and more people have come to do physical training in sports clubs or other health promotion facilities and/or in homes of individuals using physical training machines such as bicycle-type ergometers, for example. Such training machines, in general, incorporate therein exercise programs like physical fitness measuring programs or physical training programs as fixed software (control programs).

Recently, along with rapid developments of medical science, exercise physiology, and soon, there is a continuous change in standard and method of physical strength estimation, and it is desired to provide users with up-to-date exercise programs making use of results of medical science, exercise physiology, and so on. On the other hand, generation of users has come to range from that of younger people to that of elderly people, and it is desired to provide optimum exercise programs meeting the purposes of exercises and physical strength levels of individual users.

With conventional physical training machines, however, users are supplied with exercise programs in form of fixed built-in software. Therefore, to introduce an up-to-date exercise program making use of results of medical science, exercise physiology, and other sciences, it is necessary to buy a new physical training machine, itself, or software, which invites a considerable expense.

Additionally, in order to cope with all users of wide age brackets that are different in purpose of exercises and physical strength level, a plurality of physical training machines as many as different kinds of built-in exercise programs have to be equipped. This results in a large running cost.

SUMMARY OF THE INVENTION

It is therefore an object of the present invention to provide a physical training machine operation system and its method adapted to present up-to-date exercise programs making use of results of medical science, exercise physiology and other like sciences, inexpensively and specifically for individual users.

According to the first aspect of the present invention, there is provided a physical training machine operation system comprising: a physical training machine; and a server connected to the physical training machine via a network and holding a plurality of different kinds of exercise programs to be used in the physical training machine, and wherein the server selects a specific exercise program from the different kinds of exercise programs in response to a request of a user, so that the selected exercise program is supplied to the physical training machine.

In the first aspect of the present invention, the physical training machine operation system preferably includes a registration device that registers a personal information datum of a user, and the server preferably selects a specific program from the different kinds of exercise programs in accordance with the personal information datum registered by the registration device. The system preferably includes an input device that inputs an identification information datum of a user, and the server preferably extracts a specific personal information datum of a user from personal information data registered by the registration device with reference to the identification information datum of the user inputted by the input device, and selects a specific exercise program from the different kinds of the exercise programs in accordance with the extracted personal information datum of the user. Also, the physical training machine operation system preferably includes an identification information carrier that carries an identification information datum of a user, and the input device preferably reads out an identification information datum of a user from the identification information carrier. The identification information carrier preferably carries accounting charge information datum together with an identification information datum of a user. Furthermore, a personal information datum registered by the registration device is preferably managed on the server. A result of use of the physical training machine by a user is preferably managed on the server as a personal information datum of the user. Additionally, the server is preferably connected to the training machine via the Internet.

According to the second aspect of the present invention, there is provided a physical training machine operation method comprising the steps of selecting a specific exercise program from a plurality of different kinds of exercise programs stored in a server in response to a request of a user that uses a physical training machine; and supplying the selected exercise program from the server to the physical training machine via a network.

In the second aspect of the present invention, the method preferably includes the step of registering a personal information datum of a user, and the selection step preferably selects a specific exercise program from the different kinds of exercise programs in accordance with the registered personal information datum of the user.

According to the present invention, since any of exercise programs stored in the server is supplied to the training machine in response to a user's request via a network, up-to-date programs making use of results of medical science, exercise physiology or other sciences can be presented inexpensively and specifically for individual users.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein:

DETAILED DESCRIPTION OF THE PREFERRED EMBODIMENTS

Embodiments of the present invention will now be explained below with reference to the drawings. FIGS. 1 through 6 are diagrams illustrating an embodiment of the physical training machine operation system according to the present invention.

First referring to FIG. 1, a network configuration of the training machine operation system according to the embodiment will be explained.

Figure 1:
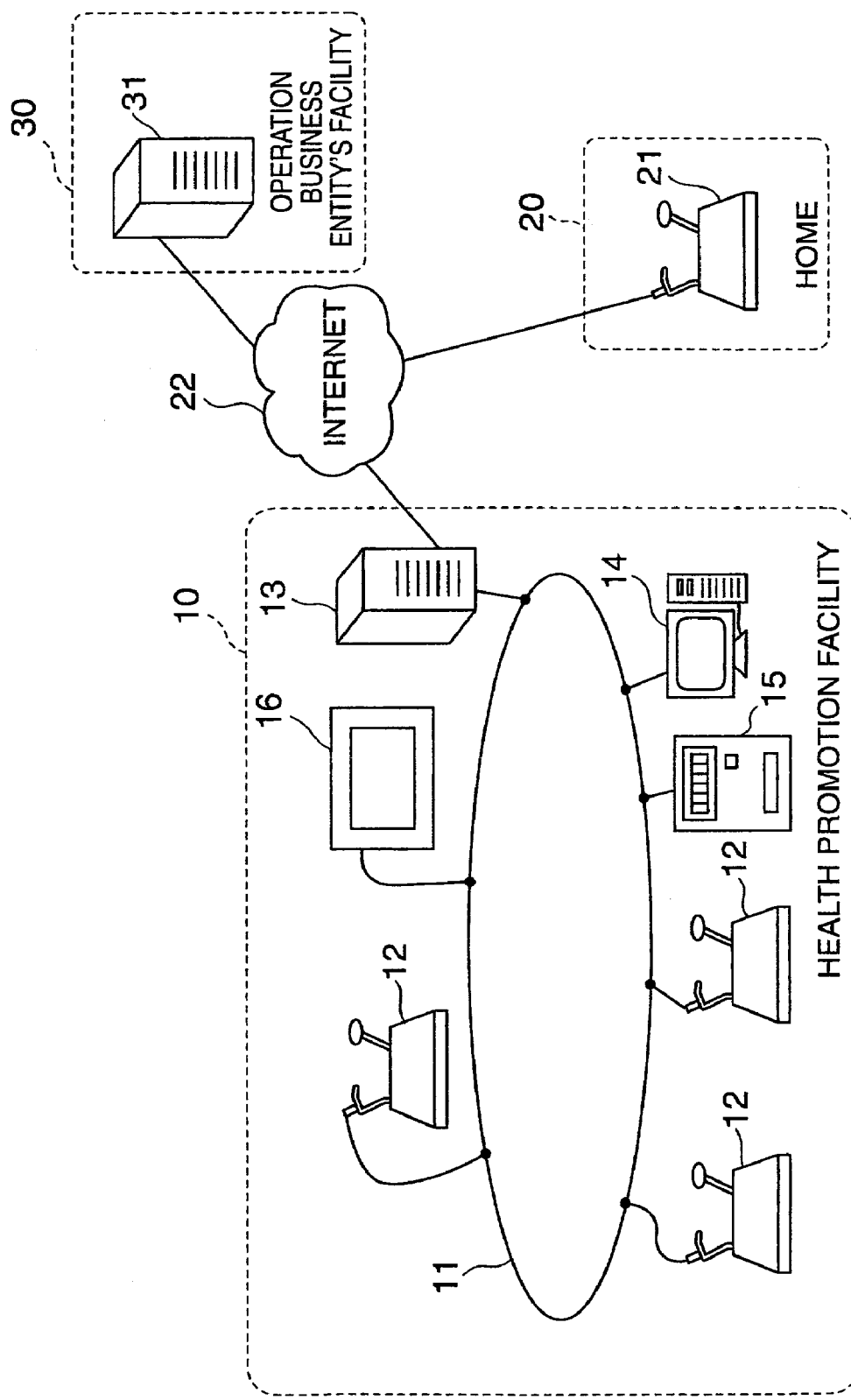
FIG. 1 is a diagram that shows a network configuration of a training machine operation system according to an embodiment of the present invention.

As shown in FIG. 1, the training machine operation system according to the embodiment is constructed by connecting various kinds of machines installed in a health promotion facility 10, home 20 and operation business entity's facility 30 altogether via an external network 22 such as Internet.

In the health promotion facility 10, a plurality of training machines 12 are installed and connected together via a private network 11 such as LAN (Local Area Network). The private network 11 includes a private server 13 connected thereto for the facility, and the respective training machines 12 connected to the private network 1 are connected to an external network 22 via the private server 13. Further connected to the private network 11 are a personal computer 14, automatic vending machine 15 and information panel 16 installed in a lobby, for example, in the health promotion facility 10.

On the other hand, a training machine 21 is installed in the home 20 and connected to the external network 22.

In the operation business entity's facility 30, a management server 31 is installed and connected to the external network 22. The management server 31 has different kinds of exercise programs (physical fitness measurement programs, training programs, and so on) to be used in the training machines 12 and 21 to select particular one of the different kinds of exercise programs in response to a user's request and supply the selected exercise program to the training machine 12 and 21 via the external network 22 and the private network 11. The exercise programs to be supplied to the training machines 12 and 21 may be in any form among software for controlling the training machines 12 and 21 (control programs), parameters used by incorporating them into such software (control programs), and control signals for controlling the training machines 12 and 21.

Figure 2:
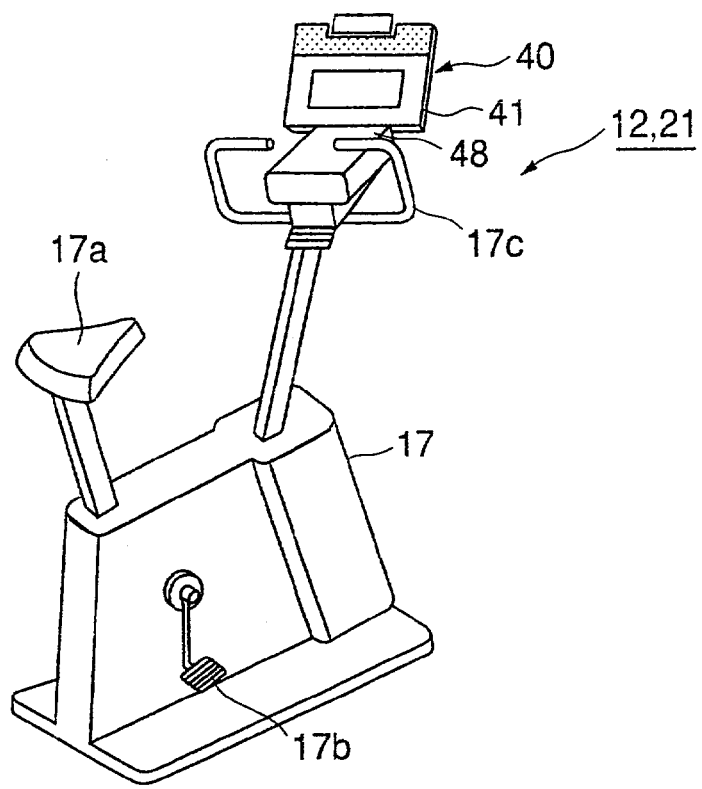
FIG. 2 is a perspective view of a training machine used in the training machine operation system shown in FIG. 1.
Figure 3:
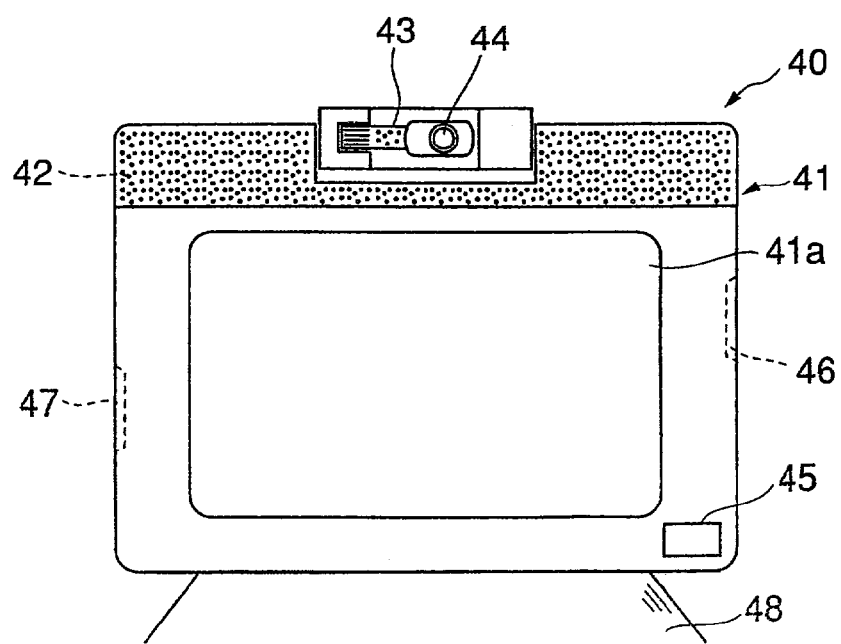
FIG. 3 is a diagram that shows the detail of a control panel of the training machine shown in FIG. 2.

FIGS. 2 and 3 are diagrams illustrating examples of training machine 12 and 21 installed in the health promotion facility 10 or individual home 20.

As shown in FIG. 2, the training machine 12 and 21 includes a training machine main body 17, and a control unit 40 mounted on an external housing of the training machine main body 17 to control behaviors of the training machine main body 17.

The training machine main body 17 shown here is a bicycle type ergometer including a saddle 17a, pedals 17b and a handle 17c like a normal bicycle as shown in FIG. 2 such that a user sitting on the saddle 17a can conduct pedaling exercise by grasping the handle 17c and operating the pedals 17b by feet. The training machine main body 17 can be adjusted in height of the saddle 17a, position of the handle 17b, and so forth, such that any user can take his/her own best posture. An electromagnetic brake-type load-generating device (not shown) is connected to the pedals 17b to apply a constant load to the user.

The control unit 40 includes, as shown in FIG. 3, a control box 48 for controlling the load-generating device (not shown) of the training machine main body 17 by using the pulse of a user detected by a pulse detector (not shown), and a control panel 41 connected to the control box 48. The control panel 41 has a touch panel 41a manipulated to input or output various data, a loudspeaker 42 for emitting an alarm sound or music to the user, a microphone 43 introducing a user's voice, or the like, and a CCD camera 44 for taking images of the user's exercising scenes. The control panel 41 includes, as an interface to the exterior, an infrared port 45, a PCMCIA (Personal Computer Memory Card International Association) card slot 46, and an Ethernet connector 47, and it is connected to the private network 11 via the Ethernet connector 47.

Since the training machines 12 and 21 shown in FIGS. 2 and 3 are connected to each other via the private network 11 and the external network 22, the system can deliver music, video, games and other contents to users under physical fitness tests or physical training with the training machines 12 and 21, or can provide various kinds of information such as guidance of the facility, current availability of machines, and so on, from the management server 31 or a specific web site on the external network 22 such as Internet via the control panel 41 of the control unit 40. Alternatively, those contents and various kinds of information can be delivered or provided by using the personal computer 14, information panel 16, or the like, connected to the private network 11. therein with a vertical guide groove 11d across a central hole 11c and a lateral guide groove 11e perpendicular to the vertical groove 11d. The vertical guide groove 11d is slightly extended outward from the inner periphery of a circular recess 11f formed in the upper portion 11a while the lateral groove 11e is extended to the inner periphery of the circular recess 11f.

As shown in FIGS. 1 to 3 and 5, the second arm member 12 has a lower portion 12a formed to contain the slide pawls 13, 14 and cam element 15 and an upper portion 12b for attachment to the frame structure of the back rest. The lower portion 12a of second arm member 12 is formed with a circular recess 12d concentric with a central hole 12c. The circular recess 12d and central hole 12c are formed in the lower portion 12a of second arm member 12 to correspond with the circular recess 11f and central hole 11c formed in the upper portion 11a of first arm member 11. The circular recess 12d of second arm member 12 is formed at its inner periphery with a pair of diametrically opposed semi-circular ratchet portions 12e.

Figure 6:
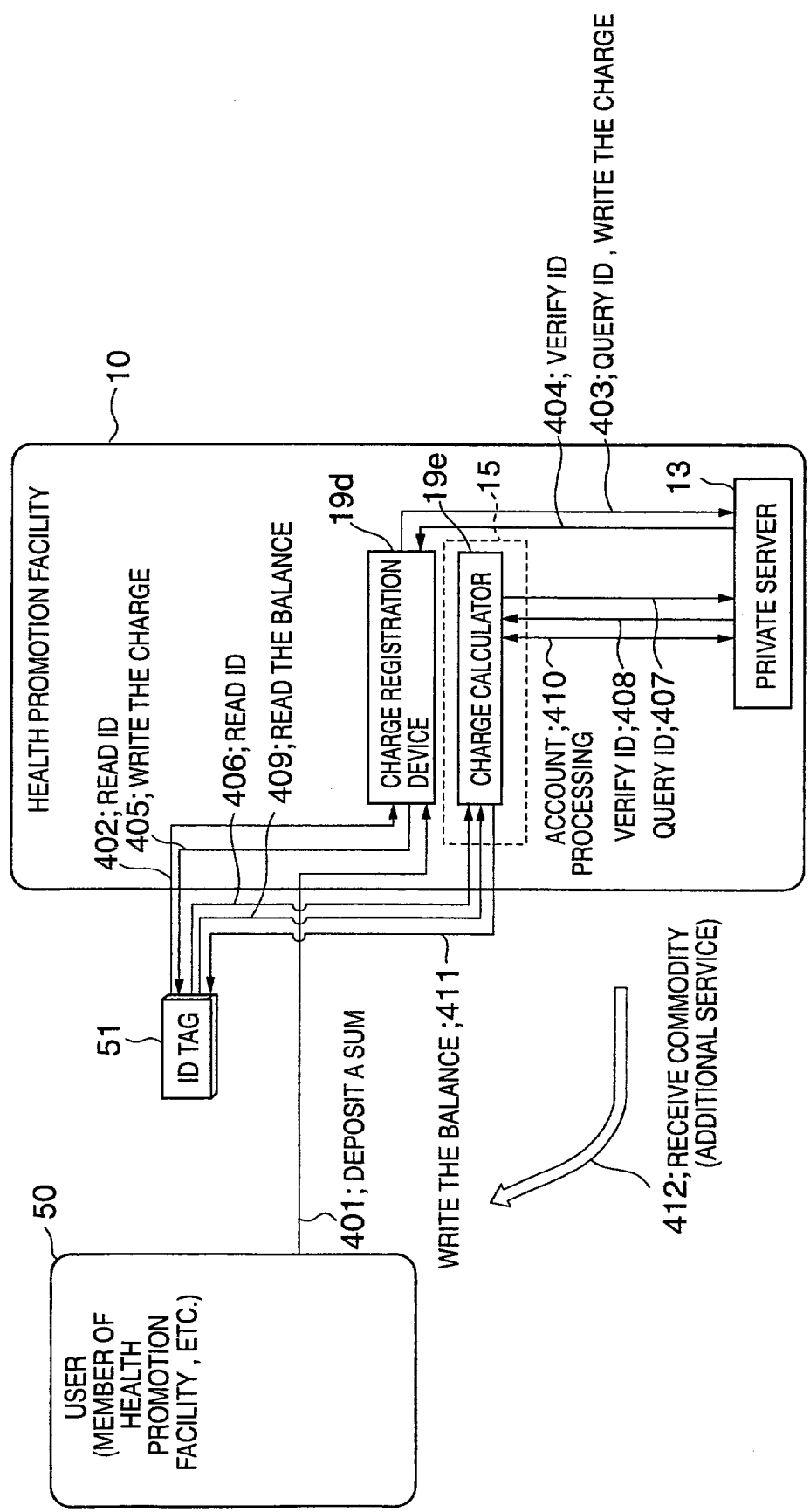
FIG. 6 is a diagram for explaining procedures of accounting processing with the training machine operation system shown in FIG. 4.

The slide pawls 13 and 13 are formed in the same width and thickness. As shown in FIG. 6, the slide pawls 13 and 14 are formed at their outer ends with semi-circular toothed portions 13a and 14a and at their inner ends with flat surfaces 13b and 14b and each pair of tapered projections 13c and 14c. The thickness of each of the slide pawls 13, 14 is determined to correspond with a space defined by the vertical guide groove 11d of first arm member 11 and the circular recess 12d of second arm member 12, and the width of each of the slide pawls 13, 14 is determined to correspond with the width of the vertical guide groove 11d of first arm member 11. The semi-circular toothed portions 13a, 14a of slide pawls 13, 14 are positioned to be engaged with and disengaged from the ratchet portions 12e of second arm member 12. The tapered projections 13c, 14c of slide pawls 13, 14 are formed to be located in the lateral guide groove 11e of first arm member 11 in a condition where the slide pawls 13, 14 are server 13 include results of the use of the training machine 12 (results of physical fitness measurement, physical training, and so on) of the users 50 in addition to their ages, genders, physical fitness levels, health conditions, exercise histories, purposes of the exercises, and so on, of the users 50. Further, based on an ID of the user 50 read out from the private server 13 by the ID read-out device 19c, personal information of a specific user is extracted from personal information of the users registered by the member registration device 19a, and an exercise program to be supplied to the training device 12 or 21 is selected in accordance with the extracted personal information of the specific user.

The private server 13 is connected to the management server 31 in the operation business entity's facility 30 under unitary management by the operation business entity via the external network 22 such as Internet. The management server 31 includes a program server 31a that holds different kinds of exercise programs such that exercise programs stored in the private server 13 in the health promotion facility 10 and exercise programs stored in the training machine 21 in the home 20 can be renewed any time. Additionally, the management server 31 includes a customers management server 31b for managing personal information of users 50 as customers data base (personal cards) to enable exchange of management information between the private server 13 in the health promotion facility 10 and the training machine 21 in the home 20 any time.

Next explained are operations of the instant embodiment having the above-explained configuration.

Figure 4:
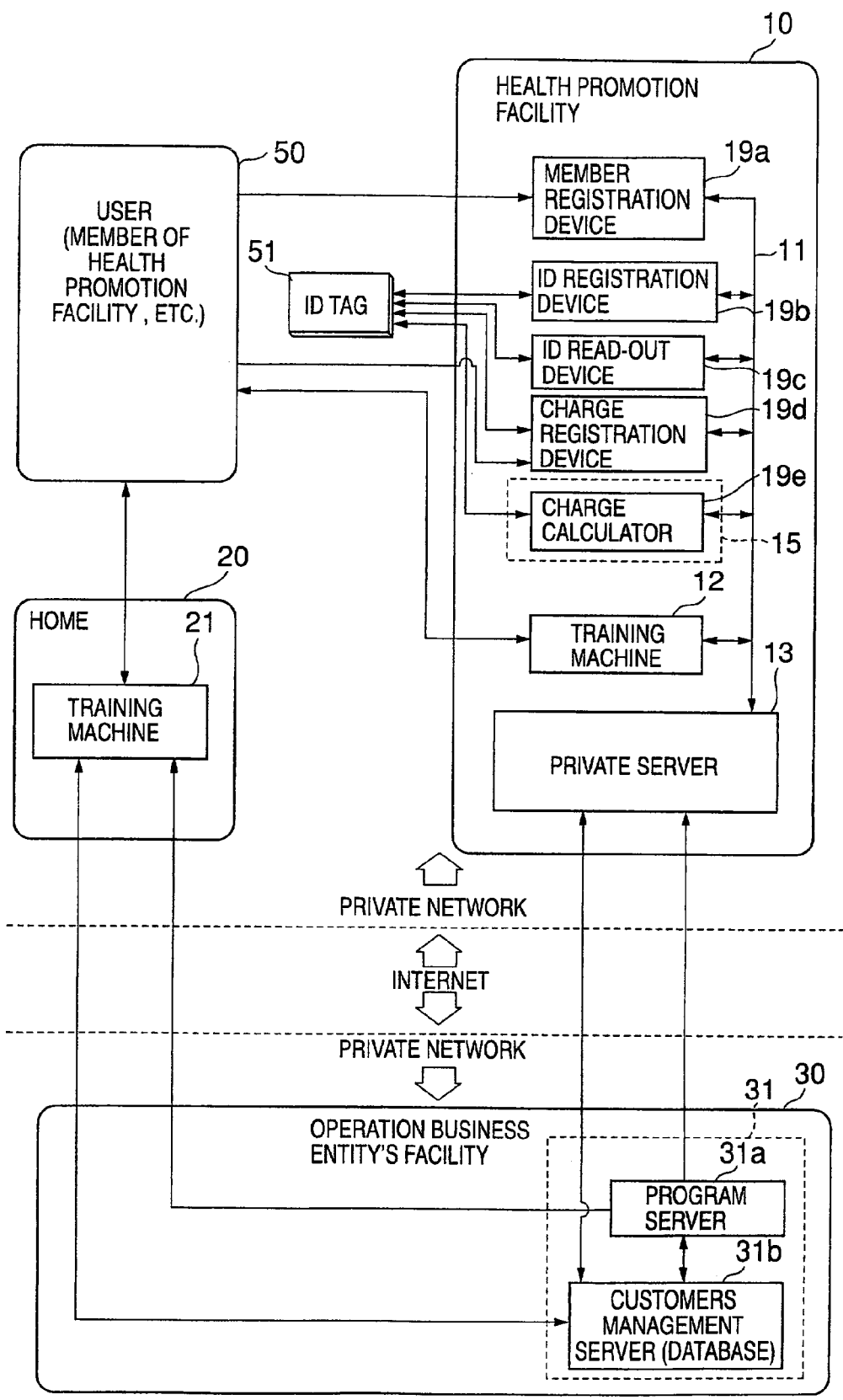
FIG. 4 is a block diagram that shows a system configuration of the training machine operation system shown in FIG. 1.
Figure 5:
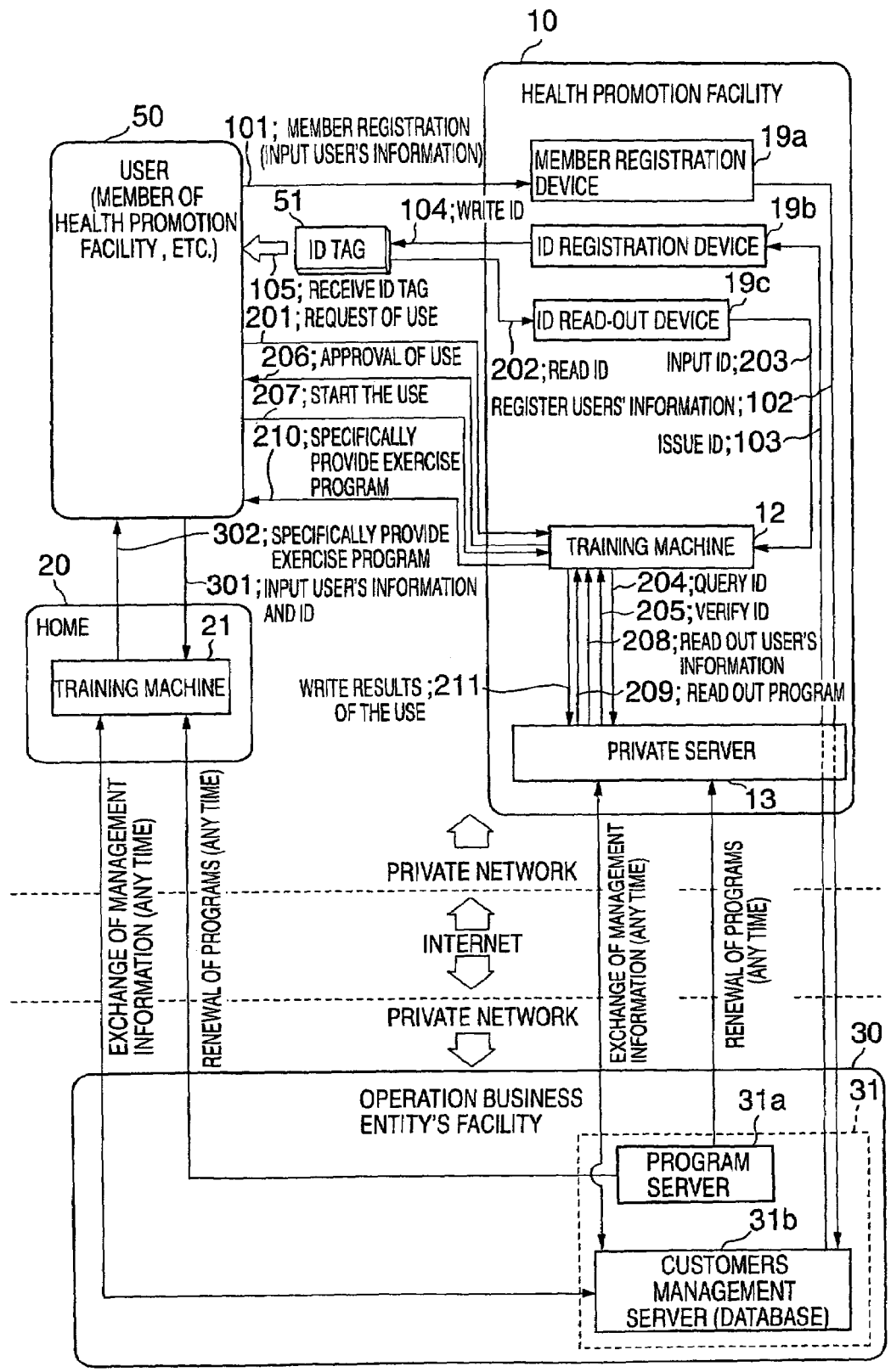
FIG. 5 is a diagram for explaining procedures of membership registration processing and training machine usage processing with the training machine operation system shown in FIG. 4.

First referring to FIG. 5, procedures of member registration processing and training machine usage processing in the health promotion facility 10 of the physical training operation system shown in FIG. 4 will be explained.

Users 50 are registered as members by registering their personal information (ages, genders, physical fitness levels, health conditions, exercise histories, purposes of exercises, and so on) by means of the member registration device 19a in the health promotion facility 10 (step 101). Thereby, personal information of the users 50 is stored as management information in both the private server 13 and the customers management server 31b of the operation business entity's facility 30 (step 102).

After that, IDs of the users 50 are issued from the customers management server 31b in the operation business entity's facility 30 (step 103), and they are written on the ID tags 51 (step 104).

The ID tags 51 with IDs of the users 50 are delivered to the respective users 50 (step 105).

After that, each user 50 having received such an ID tag 51 inputs his/her use request to the training machine 12 through the control unit 40 of the training machine 12 (step 201). Simultaneously, the user 50 connects his/her ID tag 51 and the control unit 40 of the training machine 12 via a non-contact interface such as infrared ray, electric wave, or the like. As a result, ID of the user 50 is read from the ID tag 51 by the ID read-out device 19c (step 202), and that ID of the user 50 is input to the training machine 12 (step 203).

Then this ID is queried and verified between the training machine 12 and the private server 13 (steps 204 and 205), and if the user 50 is an authorized user, the use of the machine is approved (step 206).

After that, once the user 50 starts the use of the training machine 12 (step 207), personal information of the user 50 is read out from the private server 13 (step 208), and a specific exercise program is read out from different kinds of exercise programs in accordance with the personal information of the user 50 read out (step 209). As a result, an optimum exercise program meeting his/her purpose of the exercise, physical fitness level, and so forth, is specifically given to the user 50, and the user 50 can do a physical fitness measurement test or training according to the exercise program given in this manner (step 210). Exercise programs stored in the private server 13 in the health promotion facility 10 are renewed any time to reflect exercise programs stored in the program server 31a in the operation business entity's facility 30 such that the private server 13 in the health promotion facility 10 always stores up-to-date exercise programs.

The result of the use of the training machine 12 by the user 50 is stored as personal information (management information) of the user 50 in the private server 13 (step 211). Management information is exchanged any time between the private server 13 in the health promotion facility 10 and the customers management server 31b in the operation business entity's facility 30.

Next referring to FIG. 5, procedures of training machine usage processing in the home 20 in the physical training machine operation system shown in FIG. 4 will be explained.

The user 50 inputs his/her personal information (age, gender, physical fitness level, health condition, exercise history, purpose of the exercise, and so on) and his/her ID to the training machine 21 in the home 20 (step 301). As a result, personal information of the user 50 is stored as management information in the training machine 21. The procedure of inputting personal information of the user 50 may be omitted if it is already stored in the management server 31 (customers management server 31b) in the operation business entity's facility 30 and in the training machine 21 in the home 20.

After that, once the user 50 starts the use of the training machine 21, a specific exercise program is read out from different kinds of exercise programs in accordance with the personal information of the user 50 stored in the training machine 21. Thus an optimum exercise program meeting with the purpose of the exercise, the physical fitness level, and so forth, of the user 50 is specifically given, and the user 50 can do a physical measurement test or training according to the exercise program given in this manner (step 302). Exercise programs stored in the training machine 21 in the home 20 are renewed any time to reflect exercise programs stored in the program server 31a in the operation business entity's facility 30 such that the training machine 21 in the home 20 always stores up-to-date exercise programs.

The result of the use of the training machine 21 by the user 50 is stored as personal information (management information) of the user 50 in the training machine 21. Management information is exchanged any time between the training machine 21 in the home 20 and the customers management server 31b in the operation business entity's facility 30.

Next referring to FIG. 6, procedures of account processing in the health promotion facility 10 in the physical training machine operation system shown in FIG. 4 will be explained.

The user 50 deposits beforehand a sum for account that will be necessary upon purchasing commodities or using pay-programs (services) through the charge registration device 19d in the health promotion facility 10. Simultaneously, the user 50 connects his/her ID tag 51 and to the charge registration device 19d via a non-contact interface such as infrared ray, electric wave, or the like. As a result, ID of the user 50 is read from the ID tag 51 by the charge registration device 19d (step 402), and this ID of the user 50 is queried and verified between the charge registration device 19d and the private server 13 (and the charge is written) (step 403). After the verification of ID (step 404), the deposited sum for account is written as charge information in the ID tag 51 (step 405).

After that, when the user 50 purchases a commodity (such as canned juice) through the automatic vending machine 15, for example, the user 50 connects his/her ID tag 51 to the charge calculator 19e incorporated in the automatic vending machine 15 via a non-contact interface such as infrared ray, electric wave, or the like. As a result, ID of the user 50 is read out from his/her tag 51 (step 406), and this ID is queried and verified between the charge calculator 19e and the private server 13 (steps 407 and 408). After the verification of ID, the balance of the account is read out from the ID tag 51 (step 409), and after account processing by the private server 13 (step 410), the balance after the account processing is written in the ID tag 51 (step 411).

After that, a commodity (such as canned juice) is delivered to the user 50 from the automatic vending machine 15 (step 412).

As explained above, according to the embodiment of the present invention, since exercise programs stored in the management server 31 in the operation business entity's facility 30 or in the private server 13 in the health promotion facility 10 are supplied to training machines 12 and 21 connected via an external network 20, for example, upon requests from users, it is possible to inexpensively provide up-to-date exercise programs making use of results of medical science, exercise physiology and other sciences, specifically for individual users 50. Thus, each user 50 can do a physical fitness measurement test or physical training according to such an up-to-date exercise program at a reasonable charge for the content of his/her actual use without being compelled to bear a high expense for purchasing a new training machine 12 or 21 itself or new software. In addition, all users 50 over a wide range of generations, different in purposes of exercises, physical fitness levels, and other factors, can be specifically coped with. Since the exercise programs stored in the private server 13 in the health promotion facility 10 are renewed any time to reflect exercise programs stored in the program server 31a in the operation business entity's facility 30, it is sufficient that the operation business entity, for example, renew the exercise programs in the program server 31a of the operation business entity's facility 30, and it is ensured that such renewed exercise programs are automatically supplied to the training machines 12 and 21 installed in the health promotion facility 10 or in the home 20.

Moreover, according to the embodiment of the present invention, since personal information of users 50 is registered in the management server 31 of the operation business entity's facility 30 or in the private server 13 of the health promotion facility 10 such that a specific exercise program is selected from different kinds of exercise programs in accordance with personal information of a particular user 50 registered, it is possible to readily provide each user without specialized knowledge with an optimum exercise program such that the user 50 can effectively conduct a physical fitness measurement test or training. Furthermore, personal information of users 50 registered beforehand can be used to automatically set the upper-limit load during the use of the training machine 12 or 21, or to limit the use of the training machine 12 or 21 itself, users 50 can safely practice the physical fitness measurement test or training.

Additionally, according to the embodiment, since personal information of users 50 is registered in the management server 31 of the operation business entity's facility 30, exercise programs and personal information of an individual user 50 can be shared in the health promotion facility 10 and the home 20, it is not necessary to input personal information of users 50 for each user 50 or each training machine 12 or 21, and rather, each user 50 can do physical fitness measurement tests or physical training similar to those of the health promotion facility in his/her home 20 or in another health promotion facility. Further, since personal information of users 50 (including results of exercises with the training machines 12 or 21) is registered in the management server 31 of the operation business entity's facility 30, whole aspects of health promotion activities of the users 50 can be held under unitary control, and can be effectively used as reference data for exercise prescription by trainers, medical practitioners, or the like, in health promotion facilities, medical organizations, or the like. If an ID read-out device is added to a personal computer, for example, set in a home, workplace or any other place, and connectable to Internet, it is possible to make reference to data including results of exercises with training machines 12 or 21 from anywhere.

Furthermore, according to the embodiment of the present invention, since each ID tag 51 for holding ID of each user 50 is configured to hold accounting charge information, the user 50 can deposit a sum of expected charge beforehand to his/her ID tag 51 to enable account processing without carrying cash for purchasing commodities or using pay programs (services) in the health promotion facility 10. Additionally, since each ID tag 51 is usable for entrance/exit management to and from the health promotion facility 10 as well, all of entrance/exit management, uses of machines, purchasing of commodities, uses of pay programs (services), and others, can be managed only with ID tags 51, thereby to contribute to laborsaving in operation of the health promotion facility 10 and to permit users 50 to dedicate themselves to health promotion activities that are true purposes of the users 50.

In the embodiment explained above, an example was taken for explanation as the charge calculator 19e being incorporated in the automatic vending machine 15; however, not limited to this, the charge calculator 19e may be incorporated in the control unit 40 of the training machine 12 or 21. As identification information carriers, the foregoing embodiment employs the ID tags 51 attached to locker keys, or the like, which the users 50 carry on themselves; however, instead of them, any desired means such as IC cards may be used.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A physical training machine operation system comprising:
   a physical training machine;
   a server connected to said physical training machine via a network, said server holding a plurality of different kinds of exercise programs to be used in said physical training machine; and
   a registration device that registers a personal information datum of a user,
   wherein said server selects a specific exercise program from said different kinds of exercise programs in accordance with the personal information datum registered by said registration device,
   wherein said server selects a specific exercise program from said plurality of different kinds of exercise programs in response to a request of a user, to supply the specific exercise program from said server to said physical training machine, and said server updates the specific exercise program stored in said physical training machine so that said physical training machine always stores an up-to-date exercise program
   wherein the personal information datum includes at least a health condition of the user prior to using the physical training machine, and
   wherein the server limits an upper-limit load of the physical training machine based on the personal information datum registered by the registration device such that the user can safely use the physical training machine.

2. The physical training machine operation system according to claim 1, further comprising an input device that inputs an identification information datum of a user,
   wherein said server extracts a specific personal information datum of a user from personal information data registered by said registration device with reference to the identification information datum the user inputted by said input device, and selects a specific exercise program from said different kinds of exercise programs in accordance with the extracted personal information datum of the user.

3. The physical training machine operation system according to claim 2, further comprising an identification information carrier that carries an identification information datum of a user,
   wherein said input device reads out an identification information datum of a user from the identification information carrier.

4. The physical training machine operation system according to claim 3, wherein said identification information carrier holds an accounting charge information datum together with an identification information datum of a user.

5. The physical training machine operation system according to claim 1, wherein a personal information datum registered by said registration device is managed on at least one of said physical training machine and said server.

6. The physical training machine operation system according to claim 1, wherein a result of use of said physical training machine by a user is managed on at least one of said physical training machine and said server as a personal information datum of the user.

7. The physical training machine operation system according to claim 1, wherein said server is connected to said physical training machine via the Internet.

8. The physical training machine operation system according to claim 5, wherein said server is connected to said physical training machine via the Internet.

9. The physical training machine operation system according to claim 6, wherein said server is connected to said physical training machine via the Internet.

10. A physical training machine operation method comprising the steps of:
    storing a plurality of different kinds of exercise programs in a server;
    selecting a specific exercise program from said plurality of different kinds of exercise programs stored in a server in response to a request of a user that uses said physical training machine;
    supplying the selected exercise program from said server to said physical training machine via a network;
    updating said selected exercise program stored in said physical training machine, so that said physical training machine always stores an up-to-date exercise program; and
    registering a personal information datum of a user,
    wherein, in said step of selecting, said specific exercise program is selected from said different kinds of exercise programs in accordance with the registered personal information datum of the user,
    wherein the personal information datum includes at least a health condition of the user prior to using the physical training machine, and
    wherein the server limits an upper-limit load of the physical training machine based on the personal information datum registered by the registration device such that the user can safely use the physical training machine.

11. A physical training machine operation system comprising:
    a physical training machine;
    a local server connected to said physical training machine via an internal network, said local server storing a plurality of different kinds of exercise programs to be used in said physical training machine;
    a remote server connected to said local server via an external network, said remote server updating said plurality of different kinds of exercise programs stored in said local server, so that said local server always stores up-to-date exercise programs; and
    a registration device that registers a personal information datum of a user,
    wherein said local server selects a specific exercise program from said plurality of different kinds of exercise programs in response to a request of a user, so that the selected exercise program is supplied to said physical training machines,
    wherein said local server selects a specific exercise program from said different kinds of exercise programs in accordance with the personal information datum registered by said registration device.
    wherein the personal information datum includes at least a health condition of the user prior to using the physical training machine, and
    wherein the local server limits a user an upper-limit load of the physical training machine based on the personal information datum registered by the registration device such that the user can safely use the physical training machine.

12. The physical training machine operation system according to claim 11, further comprising an input device that inputs an identification information datum of a user,
    wherein said local server extracts a specific personal information datum of a user from personal information data registered by said registration device with reference to the identification information datum the user inputted by said input device, and selects a specific exercise program from said different kinds of exercise programs in accordance with the extracted personal information datum of the user.

13. The physical training machine operation system according to claim 12, further comprising an identification information carrier that carries an identification information datum of a user,
wherein said input device reads out an identification information datum of a user from the identification information carrier.

14. The physical training machine operation system according to claim 13, wherein said identification information carrier holds an accounting charge information datum together with an identification information datum of a user.

15. The physical training machine operation system according to claim 11, wherein a personal information datum registered by said registration device is managed on at least one of said local server and said remote server.

16. The physical training machine operation system according to claim 11, wherein a result of use of said physical training machine by a user is managed on at least one of said local server and said remote server as a personal information datum of the user.

17. The physical training machine operation system according to claim 11, wherein said local server is connected to said physical training machine via a local area network, and said local server is connected to said remote server via the Internet.

* * * * *